(12) United States Patent
Kirk et al.

(10) Patent No.: US 10,492,910 B2
(45) Date of Patent: Dec. 3, 2019

(54) IMPLANTABLE VALVE AND METHOD

(71) Applicant: VENARUM MEDICAL, LLC, Fair Haven, NJ (US)

(72) Inventors: Taylor Kirk, Eatontown, NJ (US); Andrew Filachek, Beachwood, NJ (US); Janet Burpee, Fair Haven, NJ (US)

(73) Assignee: VENARUM MEDICAL, LLC, Fair Haven, NJ (US)

( * ) Notice: Subject to any disclaimer, the term of this patent is extended or adjusted under 35 U.S.C. 154(b) by 60 days.

(21) Appl. No.: 15/306,121

(22) PCT Filed: Jun. 30, 2016

(86) PCT No.: PCT/US2016/040317
§ 371 (c)(1),
(2) Date: Oct. 24, 2016

(87) PCT Pub. No.: WO2017/065850
PCT Pub. Date: Apr. 20, 2017

(65) Prior Publication Data
US 2017/0196692 A1    Jul. 13, 2017

Related U.S. Application Data

(60) Provisional application No. 62/284,923, filed on Oct. 13, 2015.

(51) Int. Cl.
*A61F 2/24* (2006.01)
*A61F 2/915* (2013.01)

(52) U.S. Cl.
CPC .......... *A61F 2/2475* (2013.01); *A61F 2/2418* (2013.01); *A61F 2/915* (2013.01);
(Continued)

(58) Field of Classification Search
CPC .... A61F 2/2418; A61F 2/2412; A61F 2/2475; A61F 2220/0058; A61F 2230/008;
(Continued)

(56) References Cited

U.S. PATENT DOCUMENTS

| | | |
|---|---|---|
| 5,330,437 A | 7/1994 | Durman |
| 6,287,334 B1 | 9/2001 | Moll et al. |

(Continued)

OTHER PUBLICATIONS

Farrell L. A. (2007). Prosthetic venous valve: Delivery and in vitro evaluation (Unpublished master's thesis). Georgia Institute of Technology.

(Continued)

*Primary Examiner* — Ann Schillinger
(74) *Attorney, Agent, or Firm* — Studebaker & Brackett PC

(57) ABSTRACT

Implantable valve for treating venous insufficiency having a self-expanding frame encased in polymer having a distal section for blood in-flow, a bulbous center section and a proximal section for blood out-flow. Polymeric leaflets have proximal ends forming a valve outlet which opens and closes in response to venous blood flow and distal portions integral with the inner polymer surface of the distal end of said bulbous section. The leaflets define a predominantly biomimetic sinus region with the bulbous section. Opening of the valve induces flushing of blood from the sinus region for smooth non-traumatic blood flow through said valve.

16 Claims, 17 Drawing Sheets

(52) U.S. Cl.
CPC .............. *A61F 2002/91575* (2013.01); *A61F 2210/0014* (2013.01); *A61F 2230/0028* (2013.01); *A61F 2230/0069* (2013.01); *A61F 2230/0076* (2013.01); *A61F 2230/0093* (2013.01); *A61F 2250/0036* (2013.01); *A61F 2250/0039* (2013.01)

(58) Field of Classification Search
CPC ...... A61F 2230/0078; A61F 2/01; A61F 2/06; A61F 2/82; A61F 2/915; A61F 2/07; A61F 2/89; A61F 2/90; A61F 2210/0076
See application file for complete search history.

(56) References Cited

U.S. PATENT DOCUMENTS

| | | | |
|---|---|---|---|
| 6,241,763 B1 | 10/2001 | Drasler et al. | |
| 6,299,637 B1 | 10/2001 | Shaolian et al. | |
| 6,458,153 B1 | 10/2002 | Boyle et al. | |
| 6,494,909 B2 | 12/2002 | Greenhalgh | |
| 6,503,272 B2 | 1/2003 | Duerig et al. | |
| 6,527,800 B1 | 3/2003 | McGuckin et al. | |
| 6,652,578 B2 | 11/2003 | Boyle et al. | |
| 6,958,076 B2 | 10/2005 | Acosta et al. | |
| 7,018,408 B2 | 3/2006 | Bailey, Sr. et al. | |
| 7,070,616 B2 | 7/2006 | Majercak et al. | |
| 7,335,214 B2 | 2/2008 | Lane et al. | |
| 7,338,520 B2 | 3/2008 | Bailey, Sr. et al. | |
| 7,347,869 B2 | 3/2008 | Hojeibane et al. | |
| 7,416,557 B2 | 8/2008 | Drasler et al. | |
| 7,479,159 B2 | 1/2009 | Camilli | |
| 7,569,071 B2 | 8/2009 | Haverkost et al. | |
| 7,604,661 B2 | 10/2009 | Pavcnik et al. | |
| 7,618,447 B2 | 11/2009 | Case et al. | |
| 7,628,803 B2 | 12/2009 | Pavcnik et al. | |
| 7,648,527 B2 | 1/2010 | Agnew | |
| 7,670,368 B2 | 3/2010 | Hill et al. | |
| 7,686,844 B2 | 3/2010 | Case et al. | |
| 7,717,930 B2 | 5/2010 | Paul, Jr. | |
| 7,780,722 B2 | 8/2010 | Thielen et al. | |
| 7,799,069 B2 | 9/2010 | Bailey, Sr. et al. | |
| 7,854,761 B2 | 12/2010 | Richardson et al. | |
| 7,951,189 B2 | 5/2011 | Haverkost et al. | |
| 8,128,681 B2 | 3/2012 | Shoemaker et al. | |
| 8,128,686 B2 | 3/2012 | Paul, Jr. et al. | |
| 8,221,492 B2 | 7/2012 | Case et al. | |
| 8,221,493 B2 | 7/2012 | Boyle et al. | |
| 8,246,676 B2 | 8/2012 | Acosta et al. | |
| 8,303,648 B2 | 11/2012 | Grewe et al. | |
| 8,303,649 B2 | 11/2012 | Agnew et al. | |
| 8,323,332 B2 | 12/2012 | Agnew | |
| 8,382,822 B2 | 2/2013 | Pavcnik et al. | |
| 8,403,979 B2 | 3/2013 | Paul, Jr. | |
| 8,460,365 B2 | 6/2013 | Haverkost et al. | |
| 8,506,620 B2 | 8/2013 | Ryan | |
| 8,591,573 B2 | 11/2013 | Barone | |
| 8,672,997 B2 | 3/2014 | Drasler et al. | |
| 8,696,737 B2 | 4/2014 | Gainor | |
| 8,721,717 B2 | 5/2014 | Shoemaker et al. | |
| 8,728,154 B2 | 5/2014 | Alkhatib | |
| 8,834,563 B2 | 9/2014 | Righini | |
| 8,992,597 B2 | 3/2015 | Pavcnik | |
| 9,028,542 B2 | 5/2015 | Hill et al. | |
| 9,078,746 B2 | 7/2015 | Pavcnik et al. | |
| 9,101,468 B2 | 8/2015 | Agnew | |
| 9,101,473 B2 | 8/2015 | Sweeney et al. | |
| 9,119,714 B2 | 9/2015 | Shandas et al. | |
| 9,301,835 B2 | 4/2016 | Campbell et al. | |
| 9,421,100 B2 | 8/2016 | Bailey, Sr. et al. | |
| 9,504,572 B2 | 9/2016 | Mauch et al. | |
| 9,474,609 B2 | 10/2016 | Haverkost et al. | |
| 2003/0023300 A1 | 1/2003 | Bailey, Sr. et al. | |
| 2003/0108588 A1* | 6/2003 | Chen | A61K 9/0024 424/423 |
| 2003/0130727 A1 | 7/2003 | Drasler et al. | |
| 2003/0171802 A1 | 9/2003 | Wilder et al. | |
| 2003/0208261 A1 | 11/2003 | Thorpe et al. | |
| 2004/0024447 A1 | 2/2004 | Haverich et al. | |
| 2004/0106976 A1 | 6/2004 | Bailey, Sr. et al. | |
| 2004/0133267 A1 | 7/2004 | Lane | |
| 2004/0193253 A1 | 9/2004 | Thorpe et al. | |
| 2004/0215339 A1 | 10/2004 | Drasler et al. | |
| 2005/0137676 A1 | 6/2005 | Richardson et al. | |
| 2005/0137681 A1 | 6/2005 | Shoemaker et al. | |
| 2006/0167543 A1 | 7/2006 | Bailey, Sr. et al. | |
| 2006/0178729 A1 | 8/2006 | Thielen et al. | |
| 2006/0178730 A1 | 8/2006 | Hill et al. | |
| 2006/0247762 A1 | 11/2006 | Acosta et al. | |
| 2006/0282157 A1 | 12/2006 | Hill et al. | |
| 2007/0038295 A1 | 2/2007 | Case et al. | |
| 2007/0050013 A1 | 3/2007 | Gross | |
| 2007/0067021 A1 | 3/2007 | Haverkost et al. | |
| 2007/0129788 A1 | 6/2007 | Drasler et al. | |
| 2007/0265699 A1 | 11/2007 | Grewe et al. | |
| 2008/0051879 A1 | 2/2008 | Case et al. | |
| 2008/0091261 A1 | 4/2008 | Long et al. | |
| 2008/0125853 A1 | 5/2008 | Bailey, Sr. et al. | |
| 2008/0161836 A1 | 7/2008 | Lane | |
| 2008/0183280 A1* | 7/2008 | Agnew | A61F 2/2418 623/1.24 |
| 2008/0275540 A1 | 11/2008 | Wen | |
| 2008/0288055 A1* | 11/2008 | Paul, Jr. | A61F 2/2412 623/1.24 |
| 2009/0105810 A1 | 4/2009 | Jaffe | |
| 2009/0248142 A1 | 10/2009 | Perkins et al. | |
| 2009/0254175 A1 | 10/2009 | Quijano et al. | |
| 2010/0005658 A1* | 1/2010 | Haverkost | A61F 2/2418 29/890.12 |
| 2010/0010614 A1 | 1/2010 | Chu | |
| 2010/0057194 A1 | 3/2010 | Ryan et al. | |
| 2010/0121423 A1 | 5/2010 | Bernhard et al. | |
| 2010/0234939 A1 | 9/2010 | Jaffe | |
| 2011/0066226 A1 | 3/2011 | Bell et al. | |
| 2011/0202124 A1 | 8/2011 | Mauch et al. | |
| 2011/0202127 A1 | 8/2011 | Mauch et al. | |
| 2011/0230949 A1 | 9/2011 | Haverkost et al. | |
| 2011/0264125 A1 | 10/2011 | Wilson et al. | |
| 2011/0319981 A1 | 12/2011 | Hill et al. | |
| 2012/0053676 A1 | 3/2012 | Ku et al. | |
| 2012/0095550 A1 | 4/2012 | Gainor | |
| 2012/0130478 A1 | 5/2012 | Shaw | |
| 2012/0143234 A1 | 6/2012 | Wilson et al. | |
| 2012/0209378 A1 | 8/2012 | Drasler et al. | |
| 2012/0289987 A1 | 11/2012 | Wilson et al. | |
| 2012/0290083 A1 | 11/2012 | Fargahi et al. | |
| 2013/0018449 A1 | 1/2013 | Bailey, Sr. et al. | |
| 2013/0018453 A1* | 1/2013 | Case | A61F 2/2418 623/1.24 |
| 2013/0060329 A1 | 3/2013 | Agnew et al. | |
| 2013/0274865 A1 | 10/2013 | Haverkost et al. | |
| 2013/0304196 A1 | 11/2013 | Kelly | |
| 2014/0012301 A1 | 1/2014 | Wilson et al. | |
| 2014/0207229 A1 | 7/2014 | Shoemaker et al. | |
| 2014/0236283 A1 | 8/2014 | Camilli et al. | |
| 2014/0257463 A1 | 11/2014 | Sweeney et al. | |
| 2014/0350666 A1 | 11/2014 | Righini | |
| 2015/0094532 A1 | 4/2015 | Wilson et al. | |
| 2015/0209146 A1 | 7/2015 | Hill et al. | |
| 2015/0216548 A1 | 8/2015 | Furuya et al. | |
| 2015/0257885 A1 | 9/2015 | McGuckin, Jr. et al. | |
| 2015/0342631 A1 | 12/2015 | Wilson et al. | |
| 2015/0366667 A1 | 12/2015 | Bailey, Sr. et al. | |
| 2016/0022421 A1 | 1/2016 | Haverkost et al. | |
| 2016/0250024 A1 | 9/2016 | Hill et al. | |
| 2017/0020672 A1 | 1/2017 | Haverkost et al. | |
| 2017/0035450 A1 | 2/2017 | Wilson | |
| 2017/0035455 A1 | 2/2017 | Wilson | |
| 2017/0065417 A1 | 3/2017 | Maleti | |

OTHER PUBLICATIONS

Pavcnik, D., Uchida, B., Kaufman, J., Keller, F., Roesch, J., (2007). Percutaneous Venous Valve Implantation in Management of Chronic

(56) References Cited

OTHER PUBLICATIONS

Deep Venous Insufficiency: An Overview of our Experimental Work and Early Clinical Experience. Ces Radiol. 61(2), 129-137.

Tien, W-H., Checn, H.Y., Berwick, Z.C, Krieger, J., Chambers, S., Dabiri, Kassab, G.S.(2014). Role of Sinus in Prosthetic Venous Valve. European Journal of Vascular and Endovascular Surgery. 48(1), 98-104.

Oberdier, Matt and Rittgers, Stanley E."The design, development, and evaluation of a prototypic, prosthetic venous valve." Biomedical Engineering Online. 7.25 (2008): 1-16.

Pavcnik, Dusan, et al. "Percutaneous management of chronic deep venous reflux: review of experimental work and early clinical experience with bioprosthetic valve." Vascular Medicine 13.1 (2008): 75-84.

Pavcnik, Dusan, et al. "Percutaneous Therapy for Deep Vein Reflux." Venous Insufficiency. Seminars in Interventional Radiology. 22.3 (2005): 225-232.

\* cited by examiner

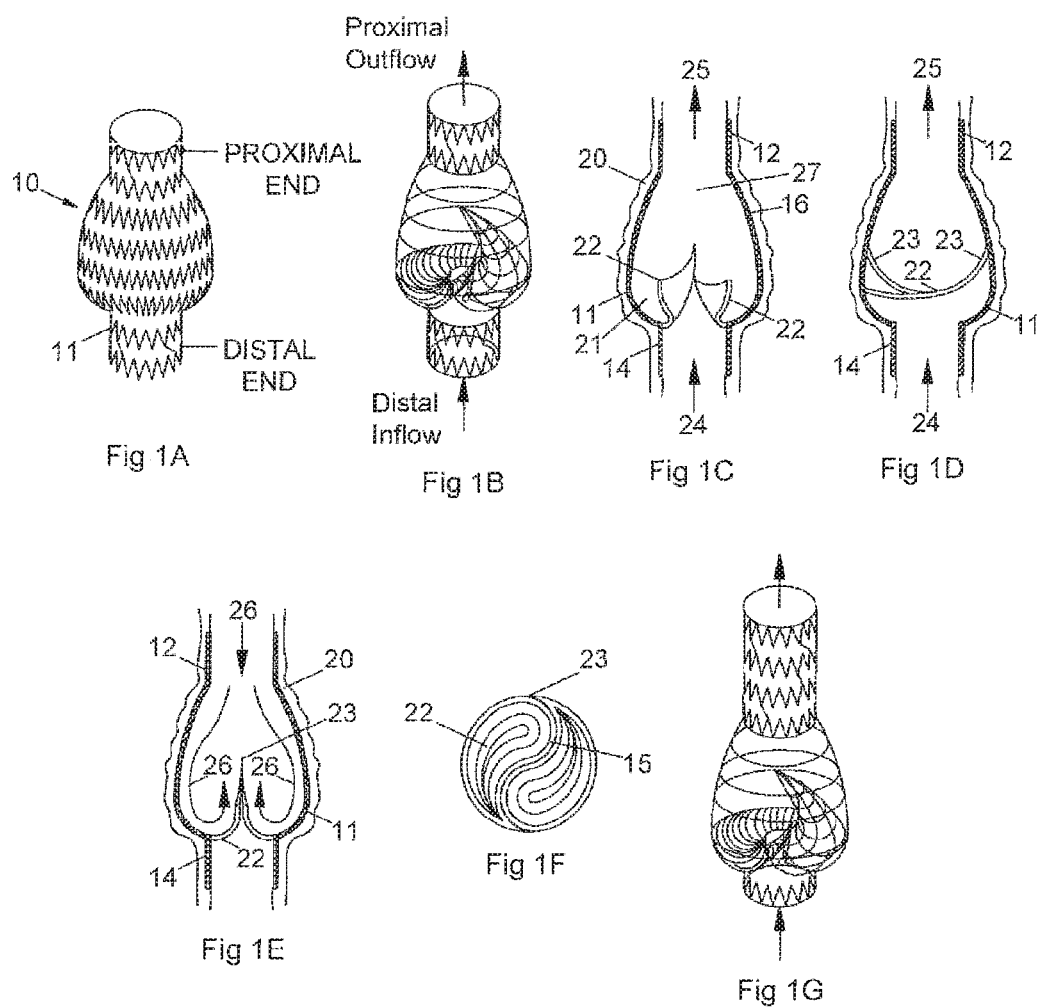

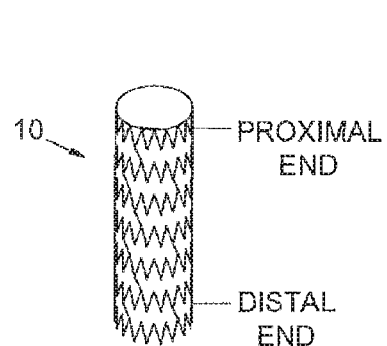
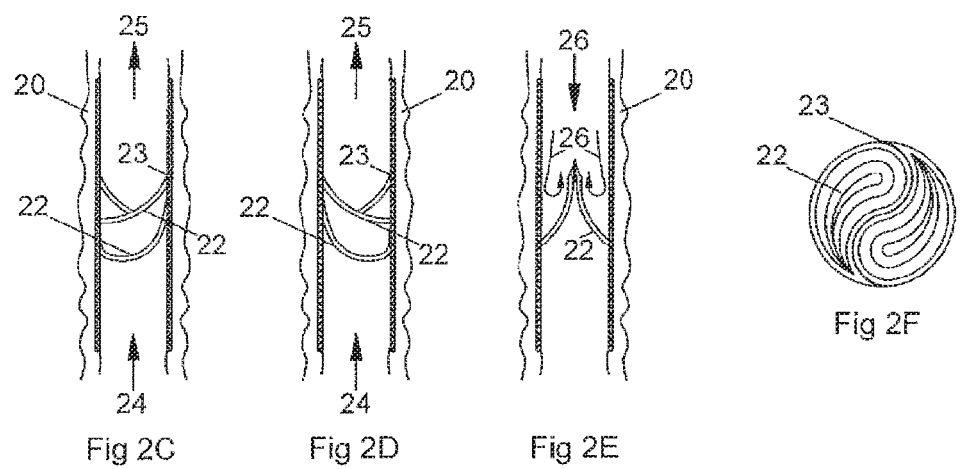

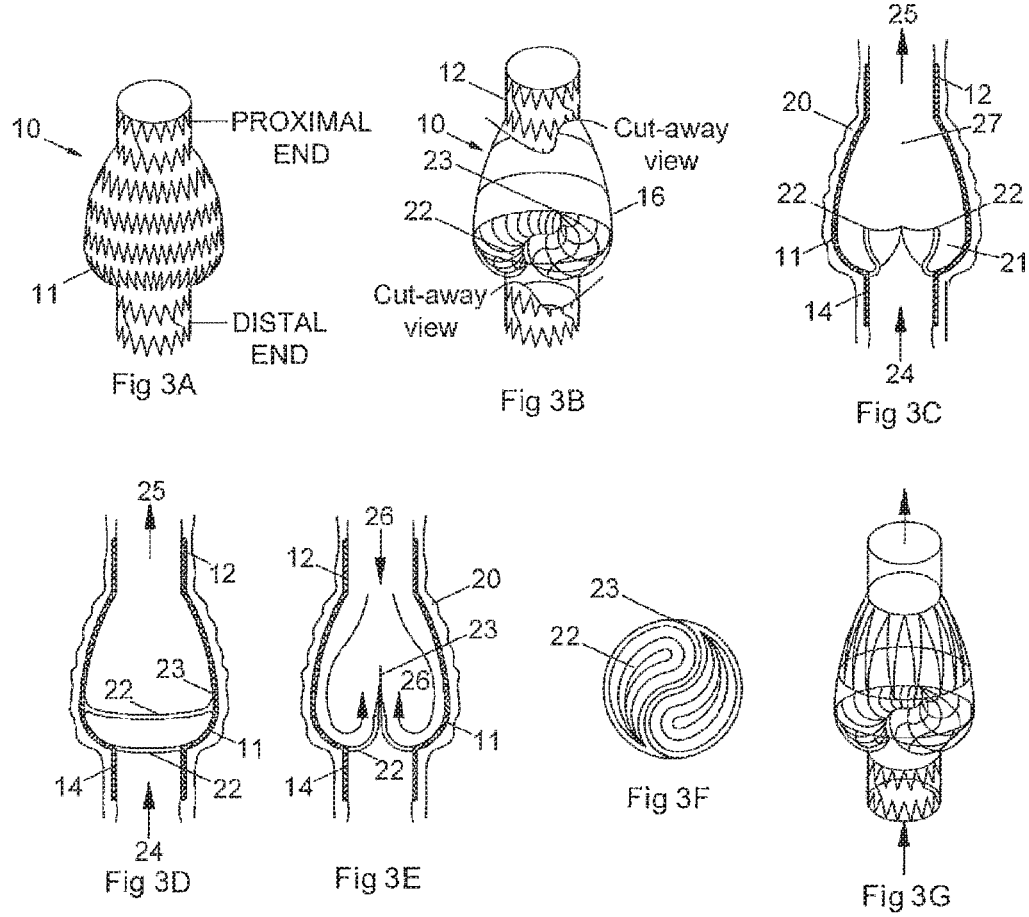

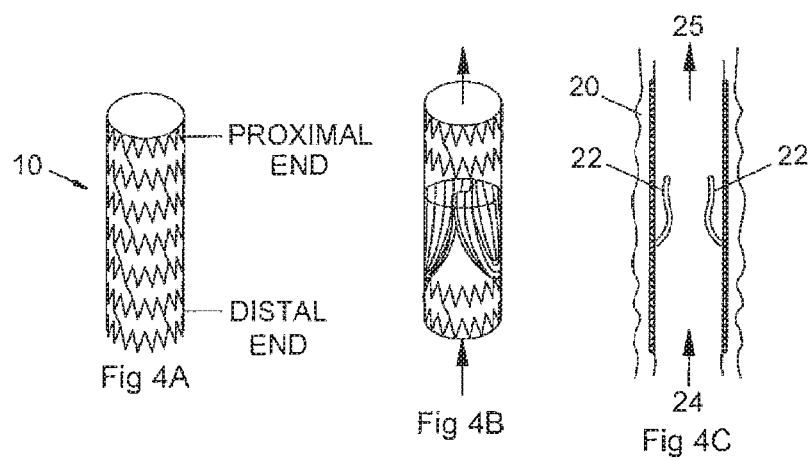
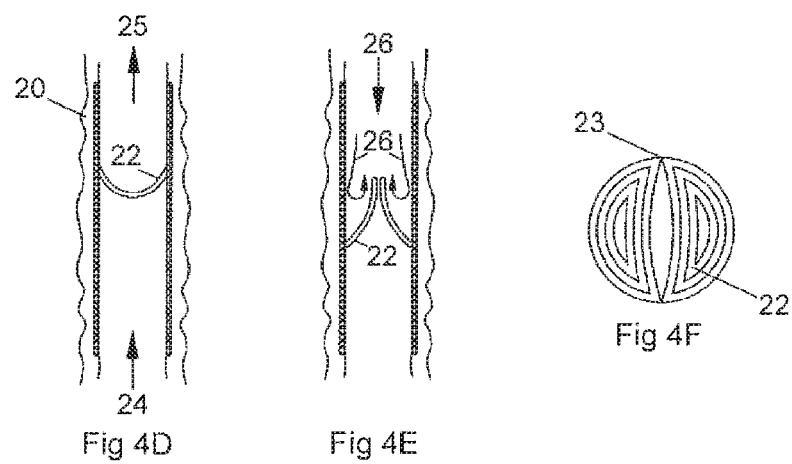

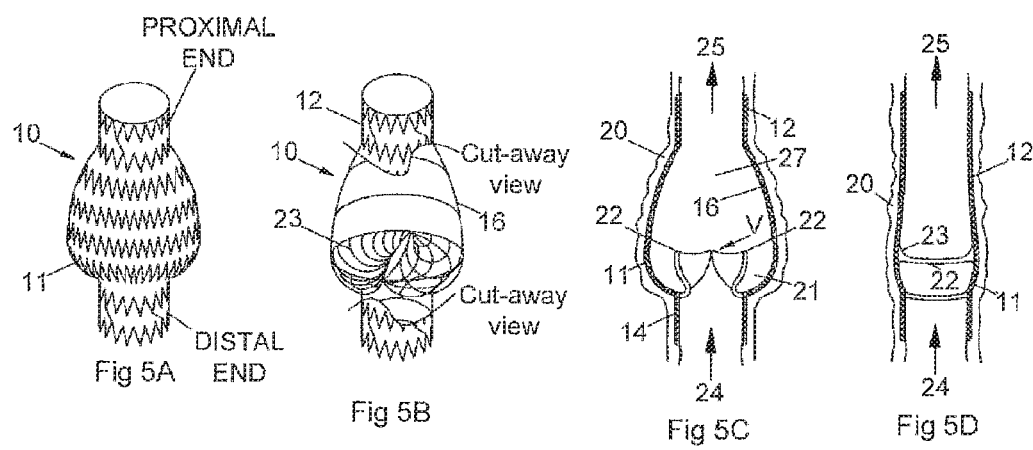
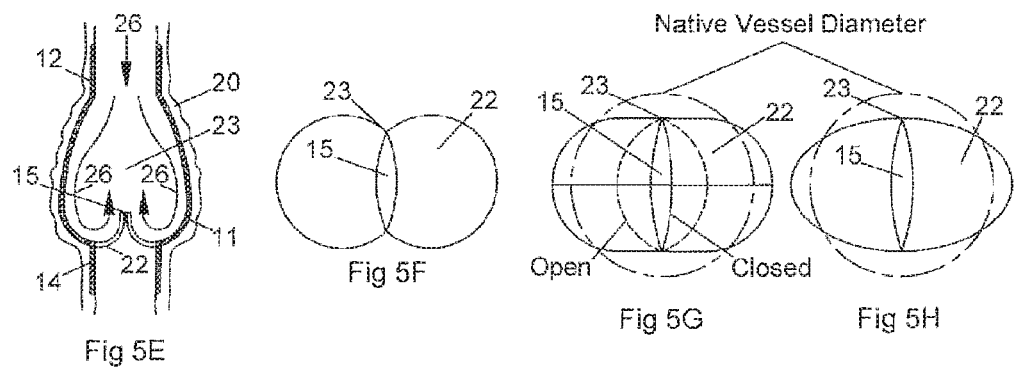

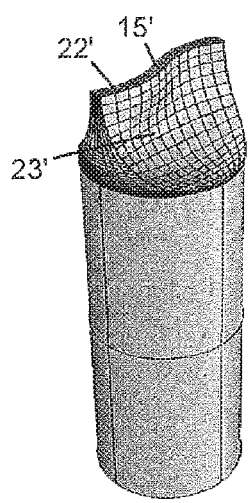
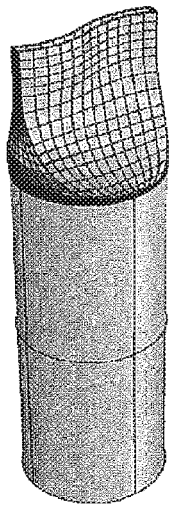
Fig 6A    Fig 6B
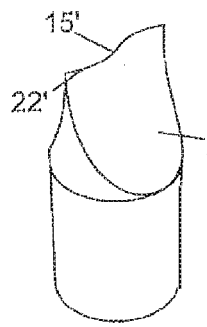
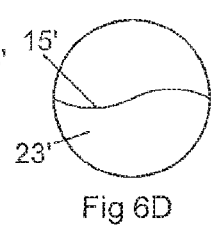
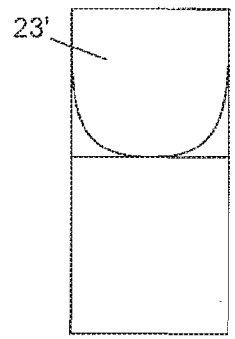
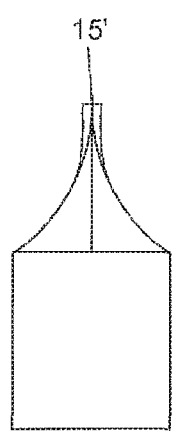
Fig 6C    Fig 6D    Fig 6E    Fig 6F

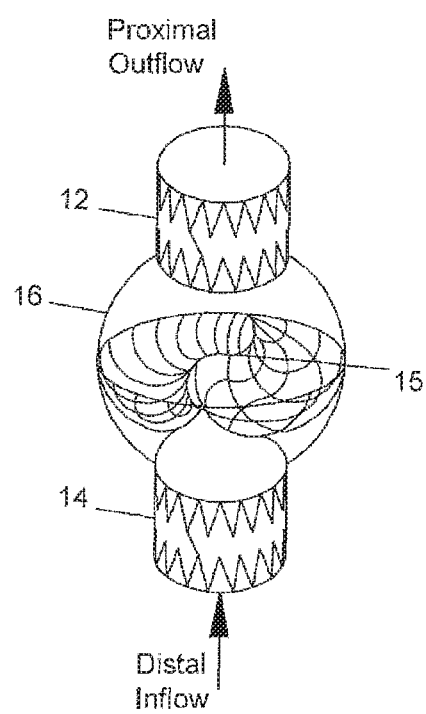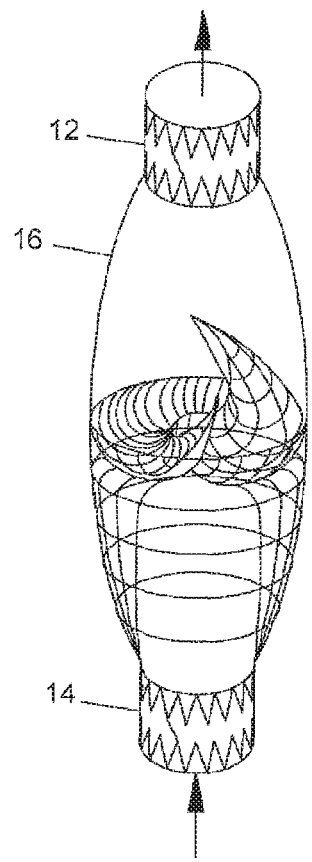
Fig 7
Fig 8

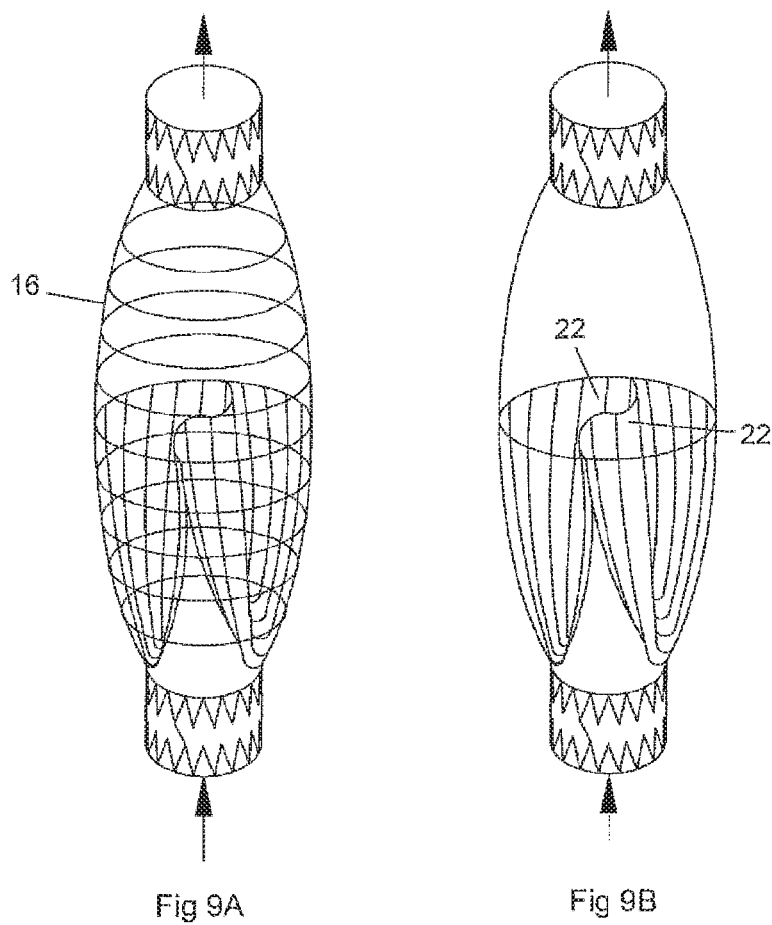

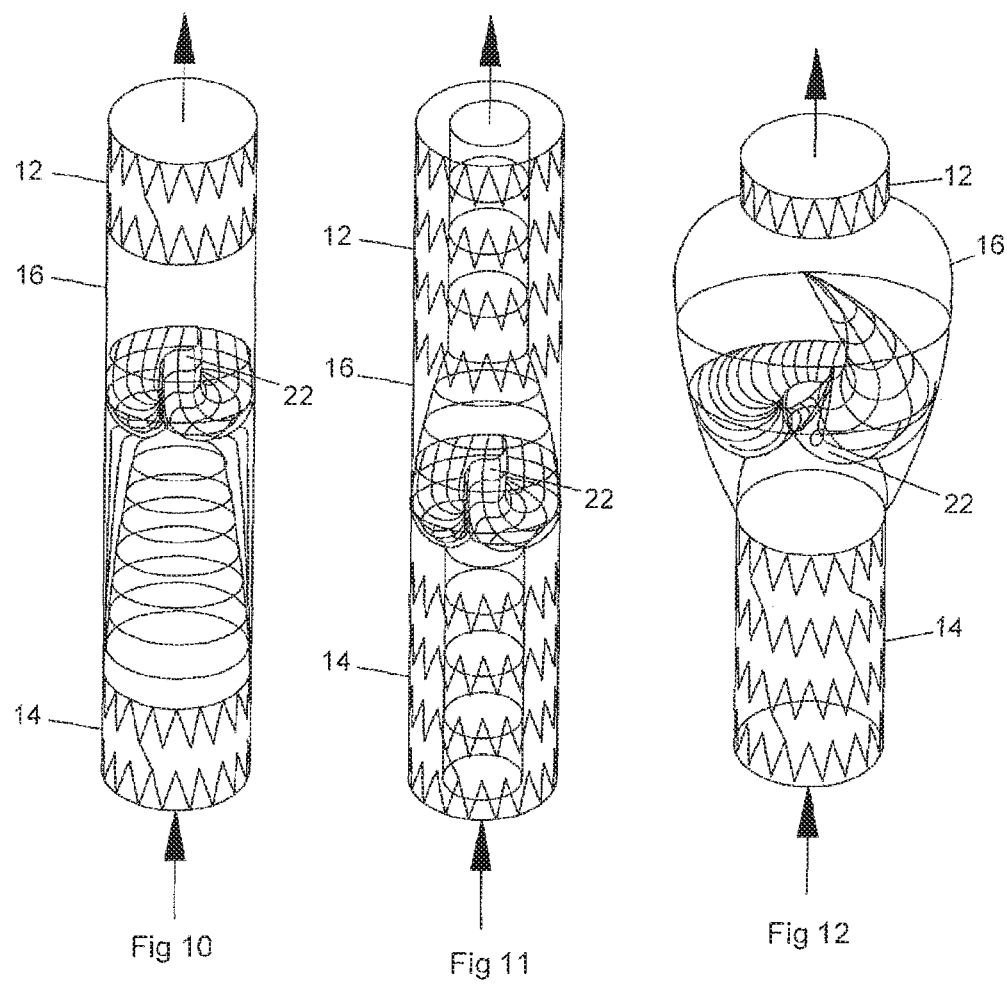

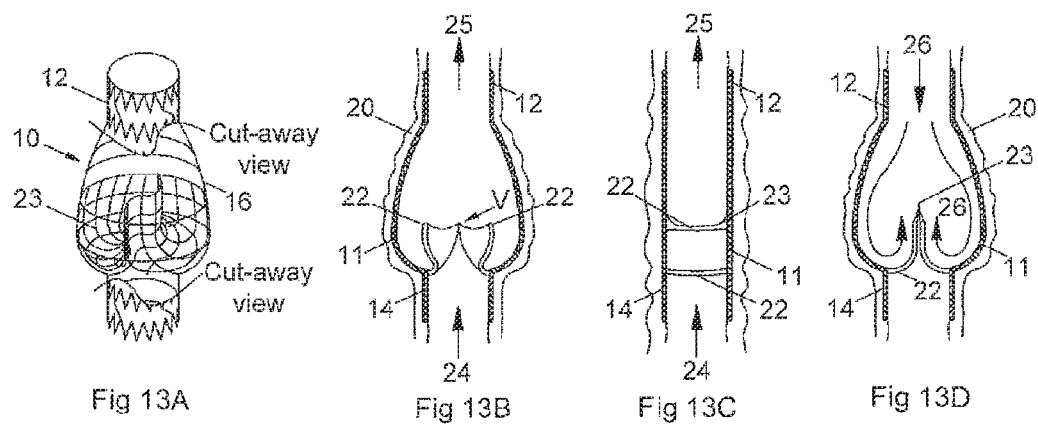
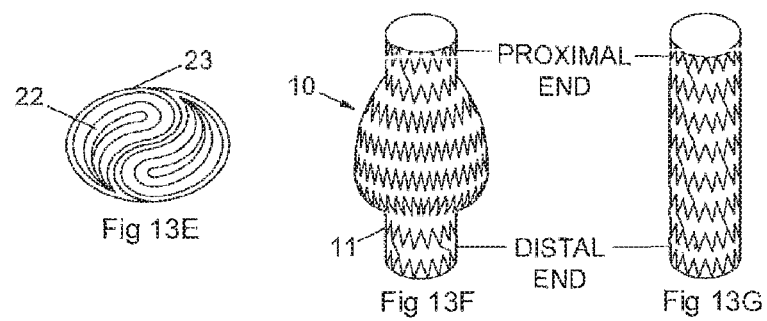

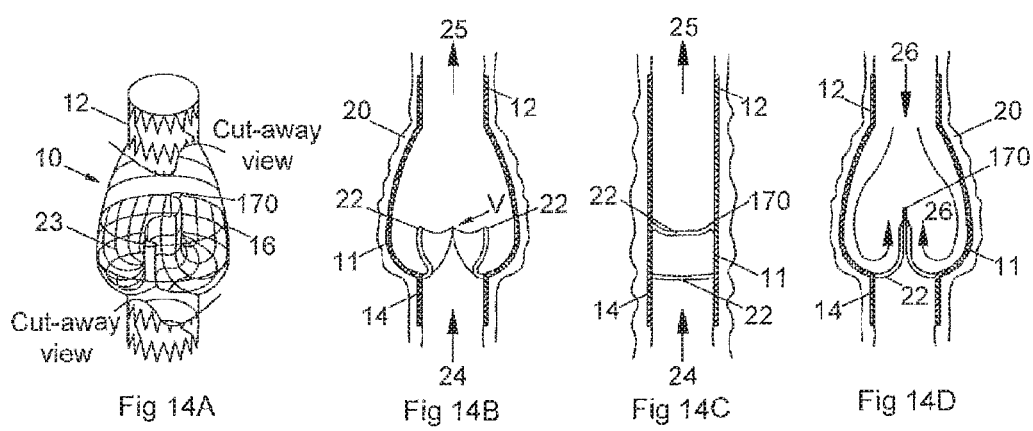
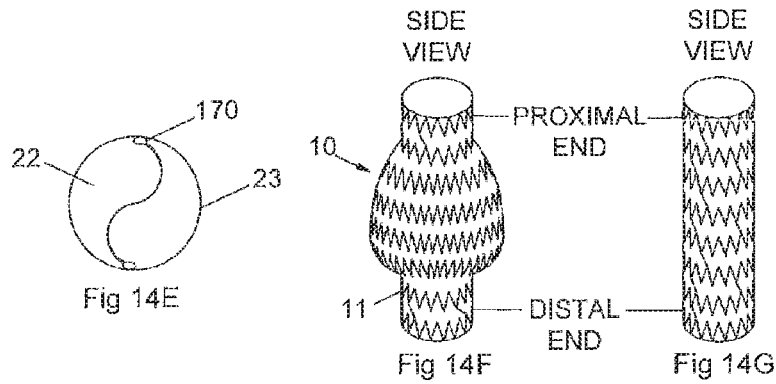

IMPLANTABLE VALVE AND METHOD

CROSS-REFERENCE TO RELATED APPLICATIONS

The present application claims priority on prior U.S. Provisional Application Ser. No. 62/284,923, filed Oct. 13, 2015, which is hereby incorporated herein in its entirety by reference.

FIELD OF THE INVENTION

This invention relates to an implantable vascular or non-vascular valve and method, and more particularly, to an implantable venous valve for treating venous insufficiency, related venous valve incompetence and method. The implantable valve enables predominantly unidirectional optimal flow of a liquid, preferably blood; it consists of a frame composed of an expandable scaffold embedded partially or fully in a biocompatible, thrombus-resistant polymer where the frame surrounds, is connected to, and is part of a functioning inner-valve. The implantable valve can be delivered endovascularly from a catheter within a vessel, and are preferably expandable from a compressed configuration to an expanded configuration.

BACKGROUND OF THE INVENTION

In the human peripheral circulatory system, veins in the leg work against gravity and pump blood towards the heart. Healthy function of venous anatomy depends strongly on a series of one-way valves that open and close, with assistance from the venous pump, a collection of skeletal muscles that aid in the circulation of blood by muscle contractions; the valves act as one-way pressure regulators to negate the effects of gravity-induced hydrostatic blood pressure, especially in the standing position where pressures of over 90 mm Hg can be experienced. When the peripheral venous system does not function properly a condition known as venous insufficiency or over a long-term, chronic venous insufficiency or CVI develops.

CVI results from either venous valve dysfunction and blood reflux; or venous obstruction due to thrombosis; or a combination of both. Venous valve reflux causes stagnant blood to pool in the leg leading to fluid/blood cell leakage into the skin and other tissues. Venous valve dysfunction is caused either primarily by congenitally weak valves; or secondarily by direct trauma, thrombosis, hormonal changes (e.g. pregnancy), and/or prolonged standing or sitting. The condition is diagnosed through physical examination, venous duplex ultrasonography, and venous air plethysmography, or less commonly by contrast venography.

CVI can manifest itself in both superficial and deep veins. Since a superficial vein is not paired with an artery, CVI in a superficial vein typically has minor health implications and can be more readily treated or removed without concern for circulatory health. A deep vein is well beneath the skin and is paired with an artery. These paired veins carry most of the blood in the body, and given their importance to circulation, are not typically removed. The risks related to untreated CVI are severe and include major injury and death from deep vein thrombosis (DVT); DVT is the formation of a blood clot in deep veins typically in the legs, thighs, or pelvis. In mild cases, CVI may cause chronic itchy skin, slight pain and swelling; in moderate to severe cases, CVI may cause lifestyle interfering edema, ulcerations and infections (cellulitis, lymphangitis).

Current CVI treatments for dysfunctional valves range from surgical reconstruction of valves to endovascular (catheter-based) technologies. Surgical correction of refluxing valves is complicated and expensive. Long-term outcomes are unpredictable and procedural risks are high. Endovascular alternatives to surgery such as venoplasty ballooning, catheter-directed lysis, and stent implantation have advanced rapidly. Although these new catheter-based techniques provide simplified treatment, their best outcomes are limited to recanalization of the vein, not minimizing venous reflux or reversing the long-term symptoms of CVI and acute DVT.

Early attempts at developing a prosthetic venous valve often led to tilting of the valve, thrombus formation at the valve, continued reflux from leaflet thickening or other problems after the valve was delivered.

SUMMARY OF THE INVENTION

The invention provides an implantable valve for treating venous insufficiency which includes an expandable scaffold, preferably self-expanding Nitinol, having a distal section for blood in-flow, a center section which contains an inner-valve and a proximal section for blood out-flow. The center section is preferably an enlarged bulbous section between the distal section and the proximal section which is adjacent the distal section and tapers towards the proximal section. The bulbous section can be annular or, preferably, non-circular wherein the widest section of the valve is wider than a given vein in one direction, and preferably about as wide as, or narrower, than a given vein when turned ninety degrees. In other words, the bulbous section in a front-rear view is wider than a vein but in a side view is about the same width as a vein and preferably narrower than a vein. The scaffold is fully or partially embedded in a biocompatible, thrombus-resistant polymer, layered polymers, or polymer with a thrombus-resistant coating, which forms a smooth inner surface throughout the distal, center and proximal sections and is substantially even with the scaffold interior without exposing same. Preferably, the scaffold is embedded in the polymer so that both its interior and exterior present smooth polymer surfaces. The polymer covered scaffold is referred herein to as the frame. The frame acts to scaffold the target vein, maintain the implantable valve shape, and anchor the implantable valve in the vein.

The inner-valve, which is the functioning valve portion of the device, is a leaflet valve which is integral with the polymer wall of the frame. The biocompatible, thrombus-resistant polymer leaflets together with the polymer wall of the frame form the space referred to as the sinus region. The inner-valve is held within the bulbous or center section of the frame, preferably in about the lower quarter adjacent to the distal section, or more in general, in the widest portion of the bulbous section. While the distal portion of the leaflet smoothly joins the frame wall, the leaflets taper from distal to proximal in thickness to increase flexibility of the inner-valve, and touch at the valve outlet when the valve is closed. The leaflets can taper continuously, in-part, or not at all.

The valve outlet is transverse to the narrower width of the bulbous center section and has a transverse width sufficient to accommodate blood flow. The valve outlet can be linear, S-shaped, helical or spiral, and the like. The space in the center section between the valve outlet and the proximal section define an upper region.

Opening and closing of the valve induces predominantly biomimetic flushing of blood from the sinus region for smooth non-traumatic blood flow through the valve with little to no stagnant flow, and therefore, a reduced risk of thrombus formation. The inner-valve material is smooth and durable to withstand the cyclic venous flow and inhibit fibrosis formation in the sinus region throughout normal opening and closing functions. Because the invention is used in diseased vessels, the intention is to mimic nature as much as possible, but possibly, not perfectly.

The invention also provides a method of treating patients with a venous insufficiency which includes loading the valve of the invention into a suitable delivery catheter and delivering the valve endovascularly to an effected venous site of a patient.

DESCRIPTION OF THE DRAWINGS

One or more of the above and other aspects, novel features and advantages of the present invention will become apparent from the following detailed description of a preferred embodiment(s) of the invention, as illustrated in the drawings, in which:

FIGS. 1A-G are perspective and cross-sectional views of an implantable valve of the invention having an annular configuration and a bulbous center section;

FIGS. 2A-F are perspective and cross-sectional views of an implantable valve of the invention having an annular configuration;

FIGS. 3A-G are perspective and cross-sectional views of an implantable valve of the invention having an annular configuration and a bulbous center section;

FIGS. 4A-F are perspective and cross-sectional views of an implantable valve of the invention having an annular configuration;

FIGS. 5A-H are perspective and cross-sectional views of an implantable valve of the invention having a non-circular bulbous center section;

FIGS. 6A and B are perspective views of preferred leaflet valves having an S-shaped valve outlet and FIGS. 6C-F and perspective and plan views of a mandrel for dip-molding the leaflet valves of FIGS. 6A and B;

FIG. 7 is perspective view of an implantable valve of the invention having an annular configuration and a bulbous center section;

FIG. 8 is perspective view of an implantable valve of the invention having an annular configuration and a bulbous center section;

FIGS. 9A-B are perspective views of an implantable valve of the invention having an annular configuration and a bulbous center section;

FIG. 10 is a perspective view of an implantable valve of the invention having an annular configuration;

FIG. 11 is a perspective view of an implantable valve of the invention having an annular configuration;

FIG. 12 is perspective view of an implantable valve of the invention having an annular configuration and a bulbous center section;

FIGS. 13A-G are perspective and cross-sectional views of an implantable valve of the invention having an annular configuration and a bulbous center section;

FIGS. 14A-G are perspective and cross-sectional views of an implantable valve of the invention having an annular configuration and a bulbous center section;

DETAILED DESCRIPTION OF THE INVENTION

Figure 15A:
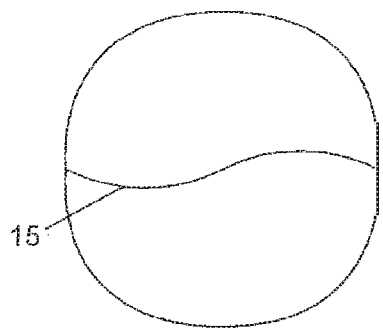
FIGS. 15A-D are perspective and plan views of a leaflet valve used in the invention.
Figure 15B:
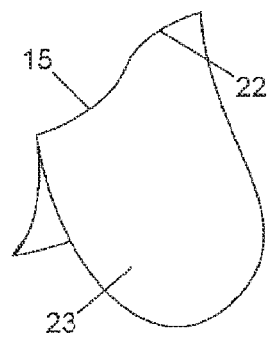
Figure 15C:
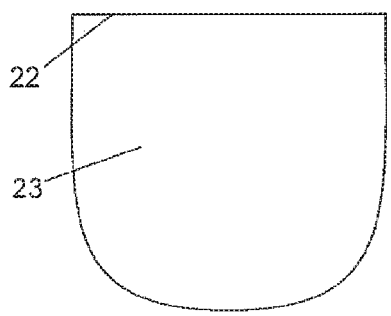
Figure 15D:
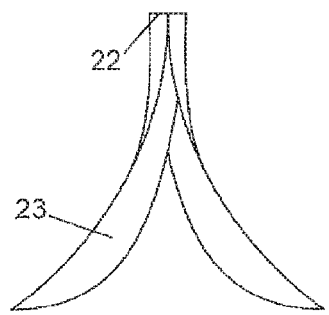
Figure 16A:
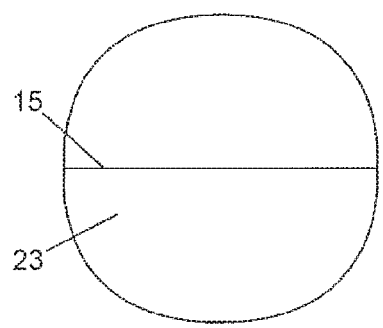
FIGS. 16A-D are perspective and plan views of a leaflet valve used in the invention.
Figure 16B:
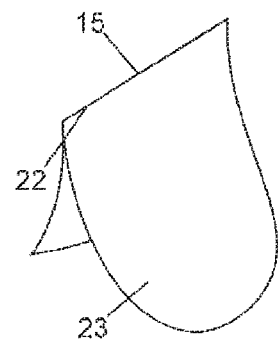
Figure 16C:
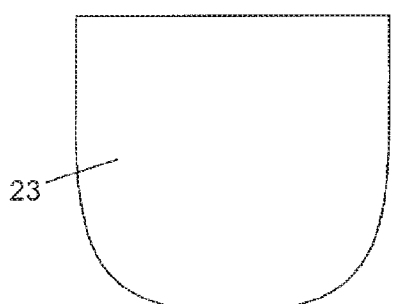
Figure 16D:
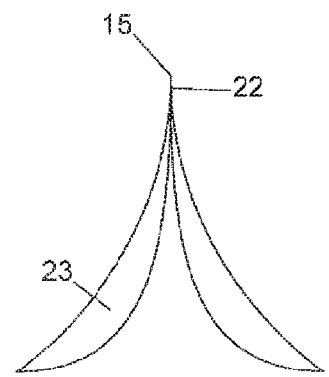

For purposes of consistency, certain terms related to the device are defined or clarified here. The following terms are used interchangeably: implantable valve and device; valve leaflet and leaflet 22; catheter and delivery system; and crimped and compressed where both refer to the device in a smaller configuration typically ready to be inserted in a catheter. The crimped device and the catheter, together form the system. Distal and proximal do not refer to the typical relationship within an artery or vein; distal refers to the inflow side or section; proximal refers to the outflow side or section. The scaffold 11 is referred to as a frame 10 when encapsulated or embedded in a polymer.

As used herein: a front-rear view refers to a view looking at the device with its widest width facing the viewer and a side lateral view is turned ninety degrees to the viewer (both views are perpendicular-views); a perpendicular-view of the device refers to a view of the device when looking at the device perpendicular to the longitudinal axis (there are infinite perpendicular views that can be seen as the device is rotated along its longitudinal axis; a given perpendicular view has a two-dimensional representations); A perpendicular or transverse plane refers to any plane intersecting the device which is perpendicular to the longitudinal axis; an axial or transverse view refers to a cross sectional-view or axial cross section of the device that is taken when sectioned perpendicular to the longitudinal axis (there are infinite axial views along the longitudinal axis); a proximal axial-view refers to an axial view from the proximal section 12; and a distal axial-view refers to an axial view from the distal section 14.

As used herein, S-shaped or linear refers to a proximal axial or transverse view of the leaflets points of contact which is also the valve outlet 15. Parallel and helical refers to the two paths the S-shape can make relative to the perpendicular plane; however, the S-shape does not have to be perfectly parallel or helical to be referred to as parallel or helical, respectively. A chord as used herein passes through the center of a given cross-section; given this definition the chord of given circle would be its diameter.

As used herein, oversizing or oversized refer to the size of the device relative to the vessel where all sections of the device are larger than the diameter of the vessel such that the vessel fits snugly around the device with no significant gaps; for example, if the distal section 14 is a tube, the diameter of the tube is larger than the average diameter of the vein 20. Oversizing can also refer to the perimeter where the perimeter of the device is greater than the perimeter of the vein 20.

Referring now to the drawings wherein like elements have the same reference numerals, FIGS. 1-5 illustrate several embodiments showing an implantable device of the invention comprising a scaffold 11 encased in a polymer or layers of polymers, together referred to herein as frame 10, which is expanded in vein 20. Frame 10 includes a distal section 14 for blood-inflow shown by arrow 24 and proximal section 12 for blood outflow (arrow 25) and a center or bulbous section 16 between sections 12 and 14. Sections 12 and 14 have an average diameter equal to or larger than the approximate inner diameter of the vein 20.

The scaffold 11 of frame 10 is embedded in a biocompatible, thrombus-resistant polymer which in one embodiment forms a smooth inner surface throughout distal, center and proximal sections 14, 16 and 12 which surface is substantially even or flush with the scaffold 11 interior without exposing same.

While scaffold 11 can be exposed on the exterior, it is preferred that a thrombus-resistant polymer form smooth inner and outer surfaces throughout the distal section 14, center section 16 and proximal section 12 which surfaces are substantially even or flush with the frame 10 interior and exterior without exposing any portion of the scaffold 11.

Center section 16 can be enlarged and bulbous adjacent distal section 14 and taper gradually towards proximal section 12 (FIGS. 1, 3 and 5). Section 16 can be approximately the same shape as distal section 14 and proximal section 12 (FIGS. 2 and 4).

Center section 16 can be annular and axially symmetrical (FIGS. 1-4) or preferably non-circular and axially non-symmetrical (FIG. 5) wherein the cross-sectional configuration at the maximum extension of center section 16 can be oval (FIG. 5H), racetrack shaped (FIG. 5G), or overlapping non-circular shapes such as egg shapes (FIG. 5F), overlapping ovals, racetracks and like non-circular shapes. The center section 16 of a valve can be wider than a natural vessel, such as a vein 20, in the front view and less wide or approximately the same width as a vessel in the side view. In one example of manufacturing, a scaffold is first formed where all three sections have the same diameter; however, in a secondary forming operation, the bulbous section 16 is formed by pinching the center section such that axial cross sections for at least part of the bulbous section 16 form a racetrack, the front view and the side view of the center section 16 are, respectively widest and narrowest as compared to the rest of the scaffold 11.

Bulbous section 16 is preferably wider than vein 20 in the front view, e.g., FIGS. 5C and E, and narrower when turned ninety degrees in the side view, preferably about the same size as vein 20 (FIG. 5D) or even narrower than vein 20.

Figure 17A:
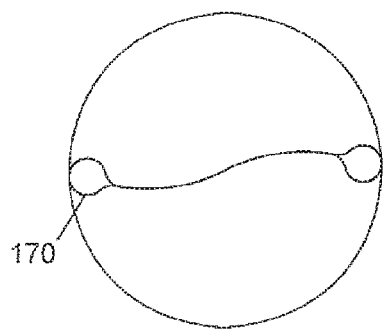
FIGS. 17A-D are perspective and plan views of a leaflet valve used in the invention.
Figure 17B:
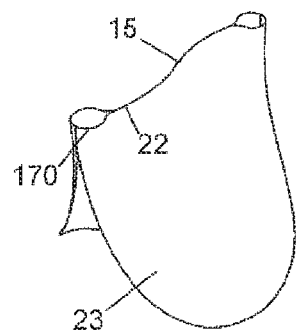
Figure 17C:
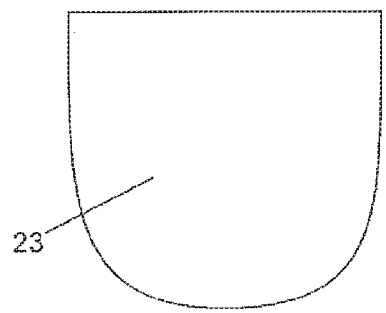
Figure 17D:
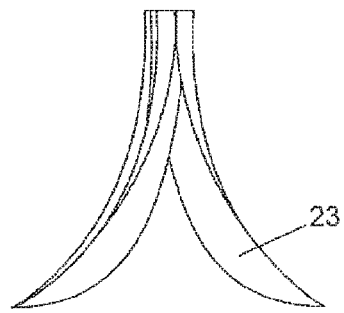
Figure 18:
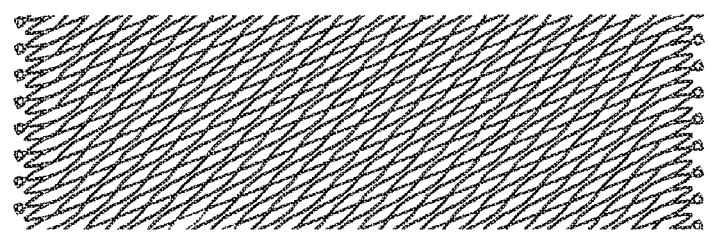
FIGS. 18-26 are plan views of several scaffold configurations that can be used in the invention.
Figure 19:
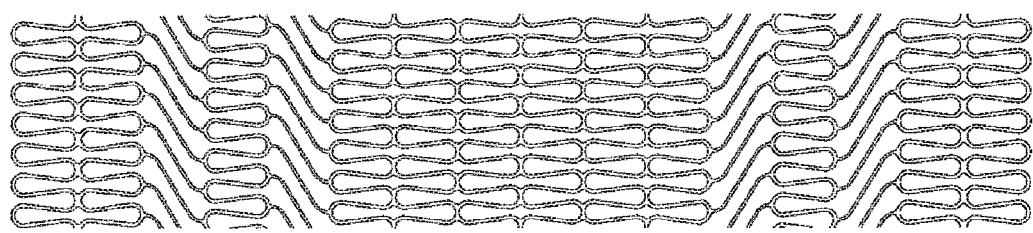
Figure 20:
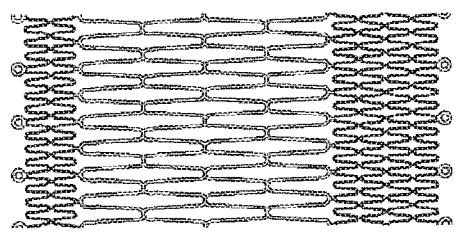
Figure 21:
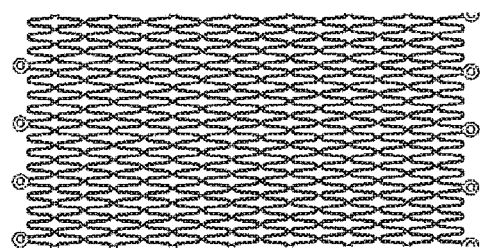
Figure 22:
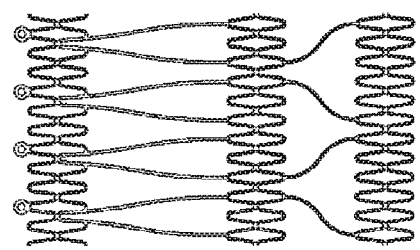
Figure 23:
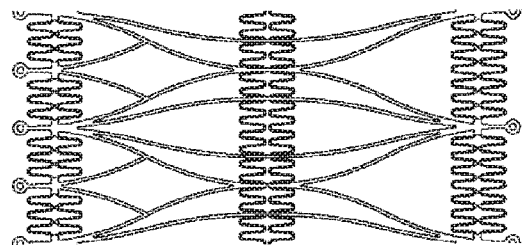
Figure 24:
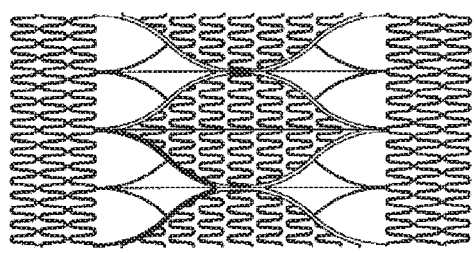
Figure 25:
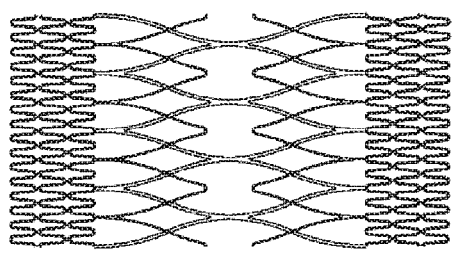
Figure 26:
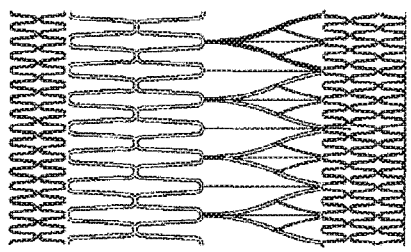

FIGS. 13 and 14 show alternate embodiments wherein bulbous section 16 is oval in cross-section (FIG. 13E) or annular (FIG. 14E) with an S-shaped valve outlet 15. FIGS. 14E and 17A-B also illustrates reflux openings 170 at the ends of valve outlet 15 to promote flushing and prevent blood stagnation. A controlled minimal reflux may be allowed to further minimize stagnate flow. One or more purposeful holes in the sinus pocket or along the valve outlet can provide minimal reflux such that blood can flow towards the distal section in considerably less volume then the flow towards the proximal section. This flow would be created to prevent stagnation.

FIG. 5D is a side view of FIG. 5C and illustrates the narrowing of the bulbous section to approximately the width of vein 20 while retaining a remnant of the bulbous configuration (FIG. 5C) where valve leaflet 23 joins the section. Compare FIG. 5D with FIGS. 13C and 14C where the bulbous section in side view is the same width as distal section 14 and proximal section 12. In FIGS. 5D, 13C and 14C, the side view of the bulbous section can be narrower at or adjacent to distal section 14. This configuration reduces the amount of blood retained in center section 16 as the valve cycles between open and closed. When narrower than a vein, there is an increase in pressure which can aid in blood flow through the valve.

FIGS. 5C-E, FIGS. 13B-D and FIGS. 14B-D illustrate another embodiment wherein leaflets 22 forming valve 15 terminate in about the lower quarter of the bulbous section thereby creating a relatively shallow sinus region 21 to minimize blood stagnation. In other words, a center line dividing bulbous section 16 will define a lower half of section 16 and valve outlet 15 will thus be in about the lower quarter of section 16, as shown.

Polymeric leaflets 22 have proximal ends that meet and form one-way valve outlet 15 which opens and closes in response to venous blood flow. The distal portion of the leaflets are connected (preferably molded) with the inner polymer surface of the distal end of bulbous section 16 or the proximal end of distal section 14.

Valve outlet 15 can be linear (FIGS. 4, 5 and 16) or preferably S-shaped (FIGS. 1-3, 6-9, and 13-15). Valve outlet 15 can also be parallel (FIGS. 3-7, 9, and 13-16), or helical (or spiral—FIGS. 1, 2, and 8). In any case, the width of valve outlet 15 will be approximate the width of a natural valve so as to allow unimpeded natural blood flow. An S-shaped outlet has a certain bias created when the valve is opened which promotes closing of the valve. FIG. 6 shows leaflets 23 of differing lengths; note the cylindrical portion becomes part of the polymer wall of the frame 10. FIGS. 6C-F illustrate mandrels that can be used to dip or spray mold valve leaflets with cylindrical portion to mold to the inner frame.

Leaflets 22, 23 are formed from a biocompatible, thrombus-resistant polymer and define a predominantly biomimetic sinus region 21 with bulbous section 16 (FIGS. 1, 3 and 5). Opening of the valve induces predominantly biomimetic flushing of blood from the sinus region 21 and biomimetic blood flow through the upper region 27 for smooth non-traumatic blood flow through said valve without thrombus formation.

FIGS. 7-12 illustrate alternate embodiments of the implantable valve. In FIG. 7, center section 16 is generally spherical and S-shaped valve outlet 15 is positioned in the center of section 16. In FIG. 8, center section 16 is elongated with the valve in the middle having a spiral configuration as in FIG. 1. The portion of center section below the inner-valve is configured to match the width of distal section 14.

FIGS. 9A-B are similar to FIG. 8 but with elongated leaflets 22 that extent from distal section 14 to about the center of section 16 forming an S-shaped outlet.

FIG. 10 illustrates an annular embodiment wherein the lower portion of section 16 tapers internally from distal section 14 towards leaflets 22 general in the center of section 16. Leaflets 22 form an S-shaped valve outlet like the valve shown in FIG. 13B. FIG. 11 is like FIG. 13 but differs in that bulbous section 16 and distal and proximal sections 14 and 12 are formed within an annular polymer frame 10. FIG. 12 is like FIG. 8 but differs in that bulbous section 16 is an inverted egg shape.

FIGS. 18-26 illustrate several patterns that are suitable for forming the scaffold 11 used to create polymer encased frame 10. It can be envisioned that all references to scaffolds 11 could refer to self-expanding scaffolds or mechanically expandable scaffolds, such as balloon expandable scaffolds. These shown are examples of scaffold designs that can facilitate the manufacturing and ultimate function of the device.

The frame 10 can be oversized relative to the vein in order to retain implantable valve to a desired site. The bulbous center section extends radially outwardly from the distal section 14; the axial cross section configuration can be annular (FIGS. 13 and 14) or preferably non-circular, such as an oval (FIG. 5H), overlapping egg-shapes (FIG. 5F), racetrack-shaped (FIG. 5G), hour-glass or similar shapes and thereafter tapers radially inward to join proximal section 12 of frame 10. FIGS. 5F-H show preferred embodiments for bulbous section 16.

The inner-valve preferably has two leaflets with a length from frame 10 wall to valve outlet equal to one-half to three distal section 14 diameters with an S-shaped outlet wherein the leaflets are parallel when closed. A tricuspid valve with three leaflets, for example, could also have S-shaped portions along three radial lines separating each leaflet.

Center section 16 contains a one-way inner-valve V at the juncture of distal section 14 and the inflow-side of bulbous section 16. Arrow 24 defines inflow to the inner-valve and arrow 25 defines outflow from the inner-valve, both for blood flow towards the heart, and arrows 26 for self-flushing flow. The self-flushing flow 26 may be closer to the outer wall of section 16 or may be closer to the valve or some combination of the two. Further the self-flushing flow 26 may be in the counter-clockwise or clockwise direction or have multiple flows that are some combination of the two. The sinus region 21 defines the location where the self-flushing flow predominantly occurs. In a preferred embodiment, the frame consists of a scaffold embedded, at least in part, within a biocompatible, thrombus-resistant polymer. The scaffold is made of a superelastic alloy such as Nitinol; The bulbous center section has an axial cross section where the minimum chord is smaller than the vein diameter, but the perimeter for that axial cross section is larger than the perimeter of the vein cross section such that the device, and in particular the bulbous section, is oversized. This embodiment may allow for a smaller opening at the valve opening enabling a local maximum of pressure. The leaflets can be tapered where it is preferred that the leaflets are each thinnest at the valve outlet to maximize flexibility at the valve outlet, and thickest at the connection to the frame to maximize durability. Further, it may be desirable to have the leaflets as short as possible while still providing adequate valve function in order to minimize possible areas of leaflet overlap, and possible areas of blood stagnation.

Usable polymers have excellent strength, elongation and durability suitable for high cycle fatigue applications in a body. The leaflets and frame polymer can be created from different polymers adjacent to one another or composed of one continuous singular polymeric material or blend. A polymer that is less thrombo-resistant may be used in conjunction with another thrombo-resistant polymer or coating that would be the primary surface for blood contact. Alternatives for creating certain aspects of the design from dip coating, spray coating or similar methods where the polymer is liquefied in a solvent, include fabrication from sheets, pre-molds or similar solid non-liquefied materials. For example, the leaflets can be cut from a polymer sheet then welded or otherwise attached to other parts of the inner-valve or frame.

Usable polymers include polyurethane or polyurethane blends, silicone or silicone blends, polycarbonate or polycarbonate blends, or layers of polymers including those to enhance anti-thombogenicity; and they can provide a smooth and hemocompatible surface which is moldable, castable, able to apply by dip coating, spray coating or similar or the like. Non-polymer materials can also be blended in with the polymer or polymers. The polymer or polymer blends can be optimized for thrombus formation resistance and to enhance endothelia cell formation. The polymers may not be specifically anti-thombogenicity if all polymers are covered with an anti-thombogenicity coating.

The expandable scaffold, and therefore, the frame and device, can be either balloon-expandable or self-expandable. If self-expandable, the expandable scaffold can made from certain elastically deformable materials or designs using certain metals such as spring steel or Nitinol, or similar including a composite of different metals; or rigid polymers such as acrylate including a composite of different polymers. Further, the expandable scaffold can be made from braided or woven wire or tube, or laser cut or machined tubing. Self-expandable and self-expanding are used interchangeably. If balloon-expandable, the expandable scaffold can be made from certain plastically or permanently deformable materials or designs using certain metals such as partially annealed stainless steel, cobalt chromium, tantalum, martensitic nickel-titanium or similar including a composite of different metals; or deformable polymers including a composite of different metals. The valve can have radiopaque markers made from tantalum, gold or platinum alloys or other radiopaque alloys or composites.

The distal section and proximal sections have some tubular length or can simply act as a small channel or opening with little or no length. The distal section and proximal sections can be different such as the distal section is tubular and the proximal section is a flare out of the bulbous section, similar to the top of a pomegranate.

The distal section can have gradients of radial strength such that the strength is greater near the center section and weaker towards the most distal end. The proximal section can have gradients of radial strength such that the strength is greater near the center section and weaker towards the most proximal end. These features could allow additional oversizing without excess stress to the vessel and/or a more gradual, less traumatic taper for best fluid flow.

In a preferred embodiment, the venous valve is crimped or compressed into a catheter and which can radially expand when deployed in a vessel as is well known in the art.

Variations of the implantable valve and system can be used in veins and other bodily vessels and is deliverable in any vessel, either vascular or non-vascular.

The invention can be used to treat venous insufficiency by:
a. providing an implantable valve such as shown in FIG. 5, 13 or 14, for example;
b. compressing the implantable device and inserting same into an intravenous delivery catheter;
c. positioning the catheter in a vein and delivering said implantable valve to a desired site in the vein; and
d. allowing implantable valve to self-expand such that frame 10 is oversized relative to a vein 20 for retention of the implantable valve in a desired site or position;

FIGS. 1, 3 and 5 show expanded bulbous section 16 wherein the vein follows the contours of the device.

Percutaneous Implantable Valve Delivery

A prosthetic implantable valve is preferably delivered from a percutaneous catheter within a body vessel. A prosthetic implantable valve is preferably adapted for transcatheter percutaneous delivery, and can be moveable from a compressed delivery state suitable for introduction to a point of treatment with a catheter delivery system, to a radially expanded implanted state for retention within the body vessel at a point of treatment therein. Radially expandable support frames include self-expandable or balloon-expandable frames. The structural characteristics of both of these types of support frames are known in the art, and are not detailed herein. The implantable valve according to the invention intended for implantation in the peripheral vasculature, such as prosthetic venous valves, advantageously include a self-expandable support frame.

While many preferred embodiments discussed herein discuss implantation of a device in a vein, other embodiments provide for implantation within other body vessels. There are many types of body canals, blood vessels, ducts, tubes and other body passages, and the term "vessel" is meant to include all such passages.

Implantable valves can be delivered into a body lumen using a system which includes a catheter. In some embodiments, implantable valves can be intraluminally delivered inside the body by a catheter that supports the implantable valve in a crimped configuration as it is transported to the desired delivery site, for example within a body vessel. Upon reaching the site, the implantable valve can be expanded and securely placed within the vessel, for example, by securely engaging the walls of the vessel lumen. The expansion mechanism may involve forcing the metal or polymer frame to expand radially outward, for example, by inflation of a balloon formed in the distal portion of the catheter, to plastically deform the frame and fix it at a predetermined expanded position in contact with the lumen wall. The expansion balloon can then be deflated and the catheter removed. In another technique, the implantable valve is formed of an elastic material that will self-expand after being crimped. During introduction into the body, the self-expanding implantable valve is restrained in the catheter lumen. When the frame has been delivered to the desired site for implantation, the restraint or sheath is removed, or similarly, the device is pushed out, allowing the implantable valve to self-expand to the lumen wall by its own internal elastic restoring force. The catheter is subsequently removed from the body by pulling it in the opposite direction in which it was delivered and leaving the expanded prosthesis in the vessel within the body.

The leaflets open to provide mechanical flushing of the outflow-side of the bulbous section to prevent thrombus formation. The open geometry provides for smooth, non-traumatic flow through the intraluminal transition and the leaflets. There can be one or more purposeful reflux openings or holes in the sinus pocket or along the S-Shape such that blood can flow towards the distal section in considerably less volume then the flow towards the proximal section. This flow prevents stagnation.

EXAMPLE

An early prototype implantable valve representative of FIG. 5 was manufactured as follows:

Tooling Fabrication
  a. A dip-coating valve mold was designed in CAD and 3D printed in ABS plastic and machined as the intended negative shape of the final expanded inside diameter of the heat-set frame, with machined and rounded features within the body intended for the valve structure. The valve mold was dipped in solvent to condition and level the surface. The valve mold was then coated in a thin layer of silicone to create a smooth, non-traumatic surface for the intended polymer material over-mold;
  b. A heat-setting mandrel was fabricated from stainless steel 10 mm rod as the intended negative shape of the final expanded valve and heat-set frame, with 8 mm ends and a 10 mm bulge in diameter and rounded features within the body for the intended valve structure and frame;

Frame Fabrication
  a. A circumferential patterned frame was designed for an integrated valve structure and radiopaque markers.
  b. The scaffold was laser cut from Nitinol tubing with a diameter between the intended crimp diameter and expanded diameter;
  c. The inside diameter of the cut scaffold pattern was surface honed;
  d. The outside diameter of the cut scaffold pattern was microblasted;
  e. The scaffold was expanded and heat-set to a 8 mm inside diameter with a 10 mm bulge feature in the frame where the intended valve structure would be attached;
  f. The scaffold was then surface finished by electropolishing;
  g. Tantalum radiopaque markers were swaged into designated features in the scaffold pattern;

Valve Fabrication
  a. A fume hood was prepared for solvent based dip coating, while the air environment was temperature and humidity controlled;
  b. A solution of 5-20% thermoplastic polyurethane (TPU) blend of urethane-polycarbonate dissolved in tetrahydrofuran was prepared and maintained in the fume hood in a 2000 mL glass container;
  c. The nitinol scaffold was partially dip coated on the distal end of the intended valve direction to encapsulate a length leading up to the intended valve position with the TPU blend;
  d. The partially dip-coated scaffold was mechanically rotated in the fume hood to distribute and level the TPU solution during the solvent evaporation leading to the TPU solidification. The partial scaffold dip coating process was repeated to fully encapsulate the scaffold (e.g. creating the frame) features in a web membrane and achieve a final cured TPU wall thickness of 2-7 mil on the frame and valve mold features. This process was conducted in <30% humidity and 20-60° C. between successive dip times<30 minutes;
  e. The partially coated scaffold was then assembled on the valve mold, specifically positioning the partially dip coated end on a supporting 8 mm diameter section, and positioning the frame with the valve mold features in relation to the heat-set frame 10 mm bulge in diameter.
  f. The valve mold and scaffold assembly was dip coated in the TPU solution in the proximal valve direction leading up to the previously dipped distal end and mechanically rotated in the fume hood to distribute and level the TPU solution during the solvent evaporation leading to the TPU solidification. This assembly dip coating process was repeated to fully encapsulate all scaffold features in a web membrane and achieve a final cured TPU wall thickness of 2-7 mil to form the final frame and valve mold features;
  g. The final coated assembly was cured at <20% Humidity and 60° C. for 24 hours, then removed from the valve mold, taking care not to damage the TPU molded valve features;
  h. An opening was cut in the molded valve features as intended for operation of the bi-leaflet valve. Excess material was trimmed from the frame and molded valve leaflets as necessary;
  i. The final, unsupported part is fully cured at <20% Humidity and 60° C. for 24-48 hours.

The prototype venous valve was radially crimped from the expanded state using both a pull-through funnel method and a radial crimp head to load the device into a 10 French, retractable catheter sheath delivery system which is comprised of an outer sheath and handle/pusher assembly. The loaded 10F catheter was positioned in an 8 mm mock vessel tube, and the device was deployed to a target position by moving the outer sheath proximally to unsheathe the device while holding the handle stationary. The polymer coated scaffold (i.e. the frame) self-expanded to oppose the inside walls of the mock vessel tube, took shape of the 10 mm bulge section, and retained the target position.

A bench top test model was assembled with mock vessel silicone tubing positioned vertically with the bottom inlet attached to a cyclic pump that would unload and allow backward flow between forward pump flow cycles, designed to provide flow and timing representative of skeletal muscle pump of a person walking A reservoir was positioned a distance above the pump to induce a head pressure representative of a person standing upright and walking. The reservoir would allow return overflow to the lower pump at a specific fill level to maintain the height and hydrostatic pressure, as to not create a syphon on the loop. The test model loop was filled with water and a prototype valve device was deployed in the mock vessel loop in a position representative of the deep veins in the leg with respect to height. Once cycled, the aqueous loop would subject the prototype to a forward flow through the valve (functionally opening), then unload. During the unloading phase, the prototype valve (functionally closing) would be subjected to a hydrostatic pressure on its proximal side, effectively testing the ability of the valve to prevent backflow or reflux. Particle dye was injected around the deployed prototype valve for visualizing the flow dynamics under test conditions.

While this invention has been described as having preferred sequences, ranges, ratios, steps, order of steps, materials, structures, symbols, indicia, graphics, color scheme(s), shapes, configurations, features, components, or designs, it is understood that it is capable of further modifications, uses and/or adaptations of the invention following in general the principle of the invention, and including such departures from the present disclosure as those come within the known or customary practice in the art to which the invention pertains, and as may be applied to the central features hereinbefore set forth, and fall within the scope of the invention and of the limits of the claims appended hereto or presented later. The invention, therefore, is not limited to the preferred embodiment(s) shown/described herein.

What is claimed is:

1. Implantable valve for treating venous insufficiency of a vein, comprising:
   a. an expandable scaffold having a distal section for blood in-flow, a center section and a proximal section for blood out-flow;
   b. said center section comprising an enlarged, non-circular and transversely symmetrical bulbous section having distal and proximal ends, said bulbous section, at its distal end, being wider than the vein in a front view and about as wide as the vein in a side view, said bulbous section tapering from its distal end towards said proximal section;
   c. said scaffold being embedded in a biocompatible polymer forming a frame which maintains the shape of said valve during opening and closing thereof, said frame having smooth inner and outer polymer walls throughout the distal, center and proximal sections;
   d. an inner-valve surrounded by and smoothly joined to said frame comprising: (i) at least two biocompatible polymeric leaflets having proximal ends transverse to the side view width of said bulbous section forming a valve outlet which opens and closes in response to venous blood flow, (ii) said leaflets having distal portions molded of one continuous polymer with the inner polymer wall of said bulbous section at its distal end such that the distal portions of said leaflets are smoothly joined to the inner polymer wall of said bulbous section, and (iii) said leaflets defining a biomimetic sinus region with said bulbous section; and
   e. wherein opening and closing of the valve induces predominantly biomimetic flushing of blood from said sinus region for smooth non-traumatic blood flow through said valve.

2. Implantable valve of claim 1 wherein said one continuous polymer is a urethane polymer.

3. Implantable valve of claim 1 wherein said bulbous section is less than the width of a vein in a side view at its distal end.

4. Implantable valve of claim 1 wherein said bulbous section is oval shaped.

5. Implantable valve of claim 1 wherein said bulbous is formed from overlapping non-circular shapes.

6. Implantable valve of claim 1 wherein said bulbous section is racetrack shaped.

7. Implantable valve of claim 1 wherein said valve outlet and said sinus region are in the lower half of said bulbous section defined by a center line dividing said bulbous section.

8. Implantable valve claim 1 wherein the frame is self-expanding nitinol, stainless steel or cobalt chromium.

9. Implantable valve of claim 1 wherein the distal portions of said leaflets taper in thickness from their integral connection with the polymer forming the inner surface of said center section to said valve outlet.

10. Implantable valve of claim 1 wherein said valve outlet is linear.

11. Implantable valve of claim 1 wherein said valve outlet is S-shaped.

12. Implantable valve of claim 1 wherein said valve outlet spirals toward the proximal section.

13. Implantable valve of claim 1 wherein said valve outlet includes reflux apertures.

14. Implantable valve of claim 1 wherein said leaflets include one or more reflux apertures.

15. Implantable valve of claim 1 wherein all sections of said valve are larger than the diameter of a vein such that the vein fits snugly around said valve.

16. Implantable valve of claim 1 wherein said proximal section flares out from said bulbous section.

* * * * *